United States Patent
Bruder et al.

(10) Patent No.: US 7,529,335 B2
(45) Date of Patent: May 5, 2009

(54) VOXEL-DRIVEN SPIRAL RECONSTRUCTION FOR CONE-BEAM COMPUTER TOMOGRAPHY

(75) Inventors: Herbert Bruder, Höchstadt (DE); Günter Lauritsch, Erlangen (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/544,291

(22) PCT Filed: Jan. 28, 2004

(86) PCT No.: PCT/EP2004/000754

§ 371 (c)(1),
(2), (4) Date: Aug. 4, 2005

(87) PCT Pub. No.: WO2004/070661

PCT Pub. Date: Aug. 19, 2004

(65) Prior Publication Data

US 2006/0140338 A1    Jun. 29, 2006

(30) Foreign Application Priority Data

Feb. 5, 2003    (DE) ................. 103 04 662

(51) Int. Cl.
  *A61B 6/00* (2006.01)
(52) U.S. Cl. ................ 378/15; 378/4
(58) Field of Classification Search ......... 378/15–20, 378/4, 210, 901
See application file for complete search history.

(56) References Cited

U.S. PATENT DOCUMENTS 5,253,171 A * 10/1993 Hsiao et al. ............... 378/4

(Continued)

FOREIGN PATENT DOCUMENTS

DE    198 43 812 A1    3/2000

(Continued)

OTHER PUBLICATIONS

A Cone-Beam Filtered Backprojection Reconstruction Algorithm for Cardiac Single Photon Emission Computed Tomography☐☐Gullberg, G. and Zeng, L.☐☐IEEE Transactions on Medical Imaging, vol. 11, No. 1 Mar. 1992.*

(Continued)

*Primary Examiner*—Edward J Glick
*Assistant Examiner*—Alexander H Taningco
(74) *Attorney, Agent, or Firm*—Harness, Dickey & Pierce (57) ABSTRACT

A method is disclosed for generating computer tomography images using a 3D image reconstruction method. According to the method, to scan an object to be examined using a cone-shaped bundle of rays originating from a focal point and a planar, preferably multi-line detector for detecting the bundle of rays, the focal point is displaced along a spiral trajectory around the object to be examined. The detector delivers output data corresponding to the detected radiation and image voxels from the scanned examined object are reconstructed from the optionally pre-processed output data, the image voxels reflecting the attenuation coefficients of the respective voxel. Each image voxel is reconstructed separately from projection data, which covers a projection angular range of at least 108° and an approximate weighting is carried out for each voxel considered in order to standardize the projection data using the voxel.

17 Claims, 4 Drawing Sheets

U.S. PATENT DOCUMENTS

| | | | | |
|---|---|---|---|---|
| 5,377,250 | A | * | 12/1994 | Hu .................. 378/15 |
| 5,430,783 | A | * | 7/1995 | Hu et al. .............. 378/15 |
| 5,708,691 | A | * | 1/1998 | Zmora ................ 378/4 |
| 5,960,056 | A | * | 9/1999 | Lai .................. 378/4 |
| 6,049,582 | A | * | 4/2000 | Navab ................ 378/4 |
| 6,118,841 | A | * | 9/2000 | Lai .................. 378/19 |
| 6,282,256 | B1 | * | 8/2001 | Grass et al. ........... 378/15 |
| 6,285,733 | B1 | * | 9/2001 | Proksa et al. .......... 378/15 |
| 6,415,013 | B1 | * | 7/2002 | Hsieh et al. ........... 378/19 |
| 6,459,754 | B1 | * | 10/2002 | Besson et al. .......... 378/4 |
| 6,477,221 | B1 | * | 11/2002 | Ning ................. 378/4 |
| 6,483,892 | B1 | * | 11/2002 | Wang et al. ........... 378/43 |
| 6,839,400 | B2 | | 1/2005 | Bruder et al. .......... 378/4 |
| 2003/0007593 | A1 | * | 1/2003 | Heuscher et al. ........ 378/4 |
| 2003/0123614 | A1 | * | 7/2003 | Silver et al. ........... 378/146 |
| 2006/0062346 | A1 | * | 3/2006 | Grass et al. ........... 378/4 |

FOREIGN PATENT DOCUMENTS

| | | |
|---|---|---|
| DE | 101 59 927 A1 | 6/2003 |
| EP | 1 096 426 A1 | 10/2000 |

OTHER PUBLICATIONS

Direct Reconstruction of Cone-Beam Data Acquired with a Vertex Path Containing a Circle☐☐Noo et al.☐☐IEEE Transactions on Image Processing, vol. 7, No. 6, Jun. 1998.*

Cone-Beam Reconstruction Using Projection-Matrices☐☐Galigekere et al.☐☐IEEE Transactions on Medical Imaging, vol. 22, No. 10, Oct. 2003.*

Kachelriess et al., 4D Reconstruction for wide cone-angle medical CT, Nuclear Science Symposium Conference Record, 2003 IEEE, vol. 5, pp. 3248-3252.*

Henrik Turbell, "Cone-Beam Reconstruction Suing Filtered Backprojection," Linköping Studies in Science and Technology—Dissertation No. 672, Linköping, Feb. 2001.

M. Kachelrieβ et al., "Advanced single-slice rebinning in cone-beam spiral CT", Med. Phys. 27 (2000) S. 754-772.

K. Stierstorfer et al., "Segmented Multiple Plane Reconstruction—A Novel Approximate Reconstruction Scheme for Multislice Spiral CT", Institute of Physics Publishing, Physics in Medicine and Biology, Phys. Med. Biol. 47 (2002), S. 2571-2581.

S. Schaller et al., "Novel Approximate Approach for High-quality Image Reconstruction in Helical cone beam CT at arbitrary pitch", Proceedings SPIE 4322 (S. 113-127).

K. Sopurbelle, Imp, Universität Erlangen, Dissertation, Prüfungsdatum 25, März 2002, Seiten 33-37.

Avinash C. Kak et al., "Principles of Computerized Tomographic Imaging", IEEE Press, New York 1987, S. 49-112.

K. Sourbelle et al, "Performance Evaluation of Exact Cone-Beam Algorithms for the Long-Object Problem in Spiral Computed tomography", Proceedings of Intern. Meeting on Fully 3-D Image Reconstruction in Radiology and Nuclear Medicine, Pacific Grove, CA USA, 10-30-Nov. 2, 2001, S. 153-156.

* cited by examiner

VOXEL-DRIVEN SPIRAL RECONSTRUCTION FOR CONE-BEAM COMPUTER TOMOGRAPHY

This application is the national phase under 35 U.S.C. § 371 of PCT International Application No. PCT/EP2004/000754 which has an International filing date of Jan. 28, 2004, which designated the United States of America and which claims priority on German Patent Application number DE 103 04 662.3 filed Feb. 5, 2003, the entire contents of which are hereby incorporated herein by reference.

FIELD

The invention generally relates to a method for generating images in computed tomography with the aid of 3D image reconstruction method. For example, it relates to one wherein, in order to scan an examination object with the aid of a conical beam emanating from a focus and the aid of a two-dimensional, preferably multirow, detector for detecting the beam, the focus is moved on a spiral focal track about the examination object. The detector supplies output data, that correspond to the detected radiation, and image voxels from the scanned examination object are reconstructed from the possibly preprocessed output data and reproduce the attenuation coefficients of the respective voxel.

BACKGROUND

Beams having cone beam geometry are known for computed tomography with multirow detectors. Reconstructing an image volume requires consideration of the cone beam geometry in the 3D image reconstruction, the cone beam geometry substantially complicating the reconstruction problem. Two different groups of image generation methods are known in principle, specifically approximate methods and exact methods:

Approximate Methods:

Approximate methods are distinguished by a high measure of practicability and flexibility. The angle of inclination of the measuring beams to the axis of rotation (cone angle) is considered in an approximate fashion, for which reason the error owing to the approximation grows with the cone angle. Starting from a certain number of detector rows, each approximate method will cause image artifacts. A distinction is made between 2D and 3D methods in the case of the approximate methods.

ASSR [1], AMPR [2] and SMPR [3] may be named as examples of the 2D method or 2D rebinning. In this case, synthetic projection data are approximated from the cone beam data, the geometry of the synthetic projection data being selected such that all the synthetic measuring beams lie in a flat plane. The object distribution in the flat plane can be reconstructed from the synthetic projection data with the aid of the conventional algorithms of 2D CT. However, with growing cone angles the approximation in the rebinning step leads relatively quickly to image artifacts.

In the case of the 3D method, filtering of the projection data and a subsequent 3D back projection are undertaken. The recorded geometry of cone beam type is taken into consideration here exactly in the back projection. Various feasible approximations are applied in the filter step. These approximation methods set forth below have in common the fact that the filtering consists of a 1D ramp filter that is aligned in the direction of the projection of the spiral tangent. The individual approximation methods differ in the processing of redundant data.

On the one hand, it is possible to average in the axial direction, as is known from [4]. Here, after the filter step the filtered projection data are back projected into the reconstruction volume such that the measured data are accumulated in weighted fashion in the process. The weights result from the axial distance of the measuring beams from the voxel to be reconstructed.

On the other hand, a reconstruction of axial slices is known from [5]. For this purpose, all the measured data that cut the image slice are used for the reconstruction. Data redundancies are considered approximately, neglecting the cone angle. Use may be made for this purpose of conventional methods such as, for example, the Parker weighting known from [6]. The filter step includes a weighting of the projection data in accordance with the present data redundancy, followed by convolution using a 1D ramp filter. This method requires a relatively large detector surface, since the projection of the entire reconstruction slice must be included on the detector for each focal position.

Exact Methods:

A comparative study of the most important exact algorithms is to be found in [7]. Exact methods consider the recorded geometry of cone beam type in a fashion free from error both in the filter step and in the 3D back projection. These methods achieve good image results independently of the cone angle that occurs. However, they are extremely complicated and very inflexible in application. For example, a reduced pitch accompanied by the employment of data redundancies can be realized only to a limited extent, and there is no possibility at all of selecting measured data for cardiac imaging with a high time resolution.

The problem now resides in that the image quality achieved and the required computational outlay are oppositely oriented as a function of the method used. Algorithms having excellent image quality in conjunction with large cone angles, that is to say for detectors with many detector rows, are essentially intended for future scanner generations. It would be desirable to avoid exact methods, since these are complicated and inflexible.

SUMMARY

It is an object of an embodiment of the invention to find in computed tomography, having multirow detectors and beams with cone beam geometry, a proposal to improve or even solve the generation of images that, on the one hand constitutes an improved or even optimum compromise between image quality and computational outlay, and on the other hand can also be applied sufficiently flexibly.

The inventors have recognized the following:

Starting from a reconstruction method such as is described in [5], instead of reconstructing entire image slices it is also possible to reconstruct the image voxels separately. Then, data redundancies are processed by using methods that permit every arbitrary projection angular range that is greater than the required half revolution π.

What aspect which is unique in at least one embodiment of the invention is the separate reconstruction of individual voxels. The projection data are weighted separately for approximate consideration of data redundancies for each individual voxel. The result of this is that, by contrast with the conventional back projection, instead of a filtered measured value being smeared along a line over all the voxels cut by the line, the measured value filtered for the voxel V is accumulated only on the voxel V.

At least one embodiment of the present invention offers at least one of the following advantages: good image quality is expected even for large cone angles, flexibility in pitch up to the theoretical maximum value, use of all the data redundancies and the possibility of data selection, for example, for cardiac imaging with high time resolution.

In accordance with this basic idea, in an embodiment of the invention the inventors propose the following method for generating images in computed tomography with the aid of a 3D image reconstruction method that has at least the following method steps:

in order to scan an examination object with the aid of a conical beam emanating from a focus and the aid of a two-dimensional, preferably multirow, detector for detecting the beam, the focus is moved on a spiral focal track about the examination object, the detector supplying output data, that correspond to the detected radiation, and image voxels from the scanned examination object are reconstructed from the possibly preprocessed output data and reproduce the attenuation coefficients of the respective voxel, each image voxel being reconstructed separately from projection data that comprise a projection angular range of at least 180°, and an approximate weighting taking place for each voxel considered in order to normalize the projection data used relating to the voxel.

Figure 4:
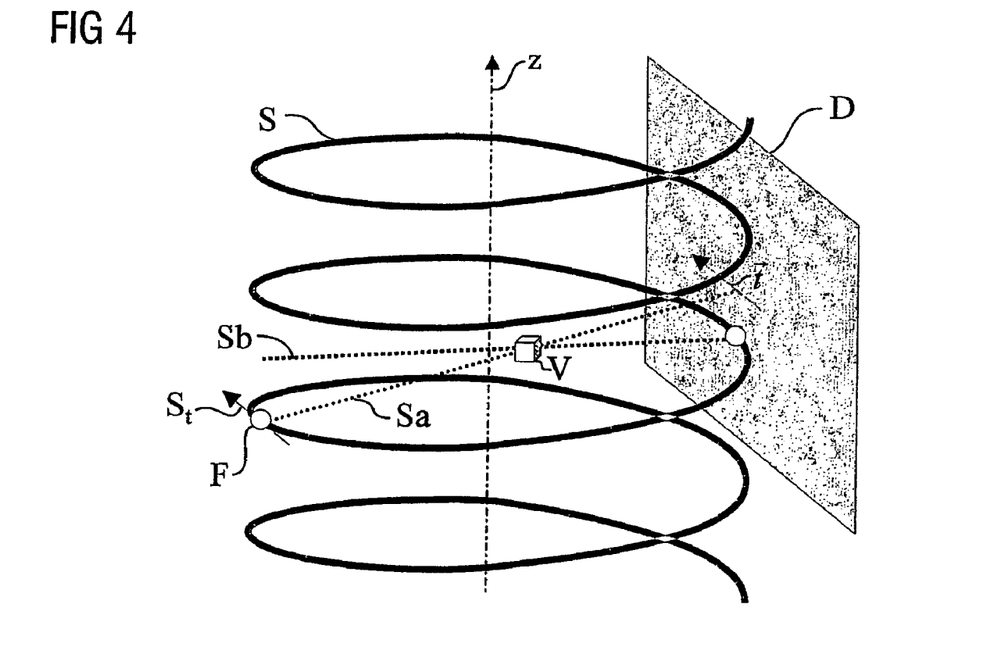
FIG. 4 shows a schematic of the collection of measured data and of the approximate redundancy of measuring beams.

It is advantageous in at least one embodiment, when—as illustrated in FIG. 4—in order to reconstruct an image voxel V, use is made of all the detector data along a straight line that runs through the cone beam projection of the voxel V and is aligned in the direction of the projection $\vec{t}$ of the spiral tangent $S_t$. An improved or even optimum detector employment is achieved thereby.

Furthermore, the image data of the detector image can be subjected to cosine weighting in order thereby to achieve a compensation of the oblique irradiation of the focus onto the detector.

If the scanning operation does not have a sufficiently high resolution in order for all the required detector data to be obtained directly for a voxel being considered, data not directly available can be obtained from the available data by interpolation from neighboring detector data (detector pixel values).

Furthermore, during the weighting for compensating the data redundancy (normalization) two measuring beams (Sa, Sb) can be regarded as redundant precisely when it holds for the parallel coordinates θ, p that: $(\theta_a = 2k \cdot \pi + \theta_b$ and $p_a = p_b)$ or $(\theta_a = (2k+1) \cdot \pi + \theta_b$ and $p_a = -p_b)$, where k represents an arbitrary natural number, and θ represents the projection angle, and the projection angle θ represents the sum of focal angle α and fan angle β, and p represents the distance from the z axis.

The redundantly available data can be multiplied by generalized Parker weights for the purpose of normalization. The normalized data are processed with the aid of a ramp filter modified by an advantageous smoothing window. It is advantageous, furthermore, when a distance weighting is performed for the 3D back projection into the voxel considered.

Finally, it is to be pointed out that the method according to at least one embodiment of the invention can also be used for cardiac computed tomography by selecting, weighting or sorting in a manner known per se the measured data in accordance with the movement phases of an examined heart, in order thus to obtain tomograms of the heart in specific movement phases.

In accordance with at least one embodiment of the invention, the inventors also propose a CT unit for scanning an examination object that is provided with a detector array that is of planar design and has a multiplicity of distributed detector elements for detecting the rays of the beam from at least one focus, the at least one focus being movable relative to the examination object on at least one focal track that runs around the examination object and a detector array situated opposite, at least a device/method for collecting detector data, filtering and 3D back projection being provided, and a device/method for processing the measured data being fashioned in such a way that the method according to at least one embodiment of the invention as outlined above can be carried out. The functional aspects are preferably implemented at least partially by programs or program modules.

BRIEF DESCRIPTION OF THE DRAWINGS

The invention is described in more detail below with reference to an example embodiment of a third-generation multirow CT unit suitable for carrying out the method according to at least one embodiment of the invention, and with the aid of the figures in which.

DETAILED DESCRIPTION OF THE EXAMPLE EMBODIMENTS

Figure 1:
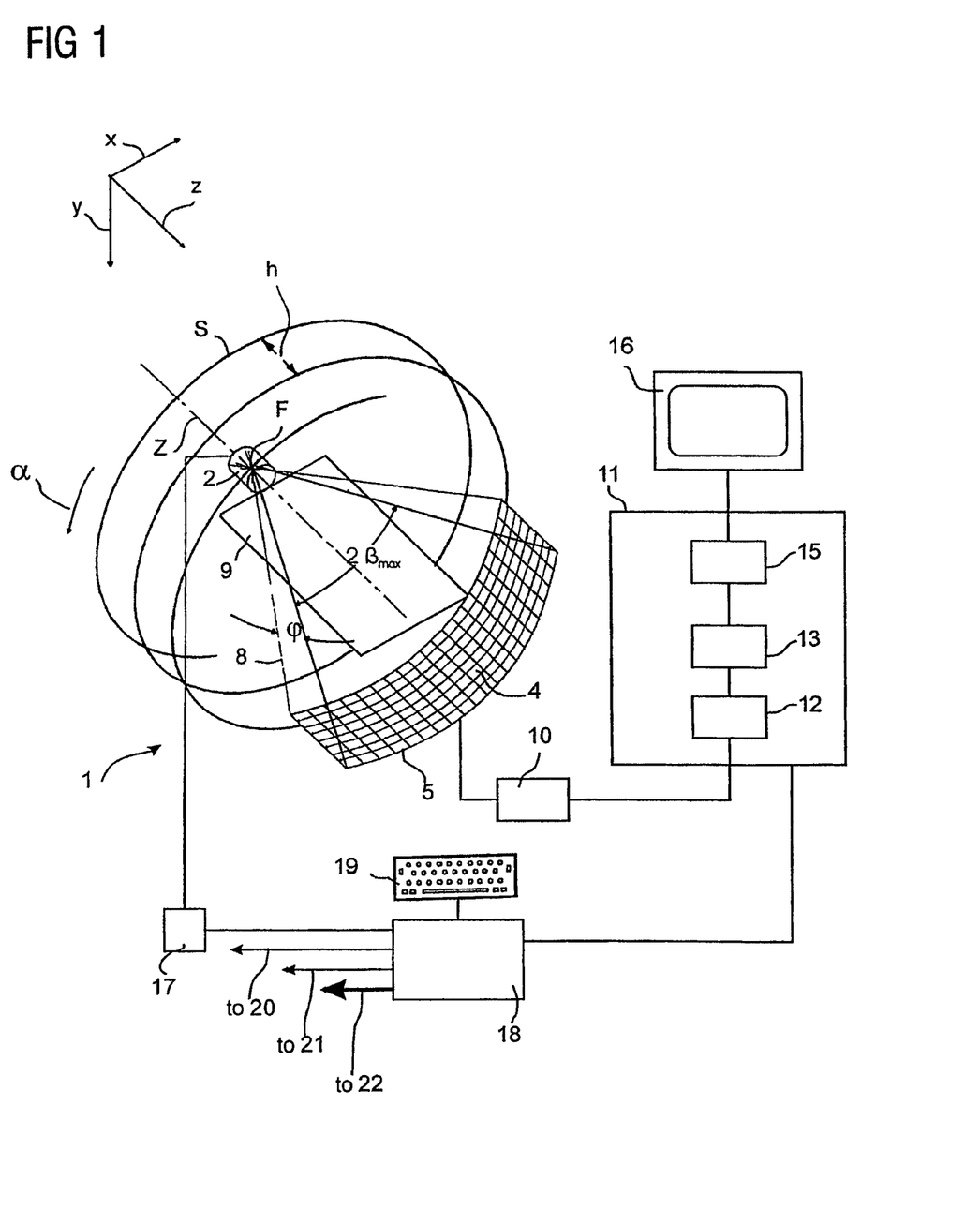
FIG. 1 shows multirow unit in a perspective illustration of the scanning unit in a schematic illustration of the peripheral equipment.
Figure 2:
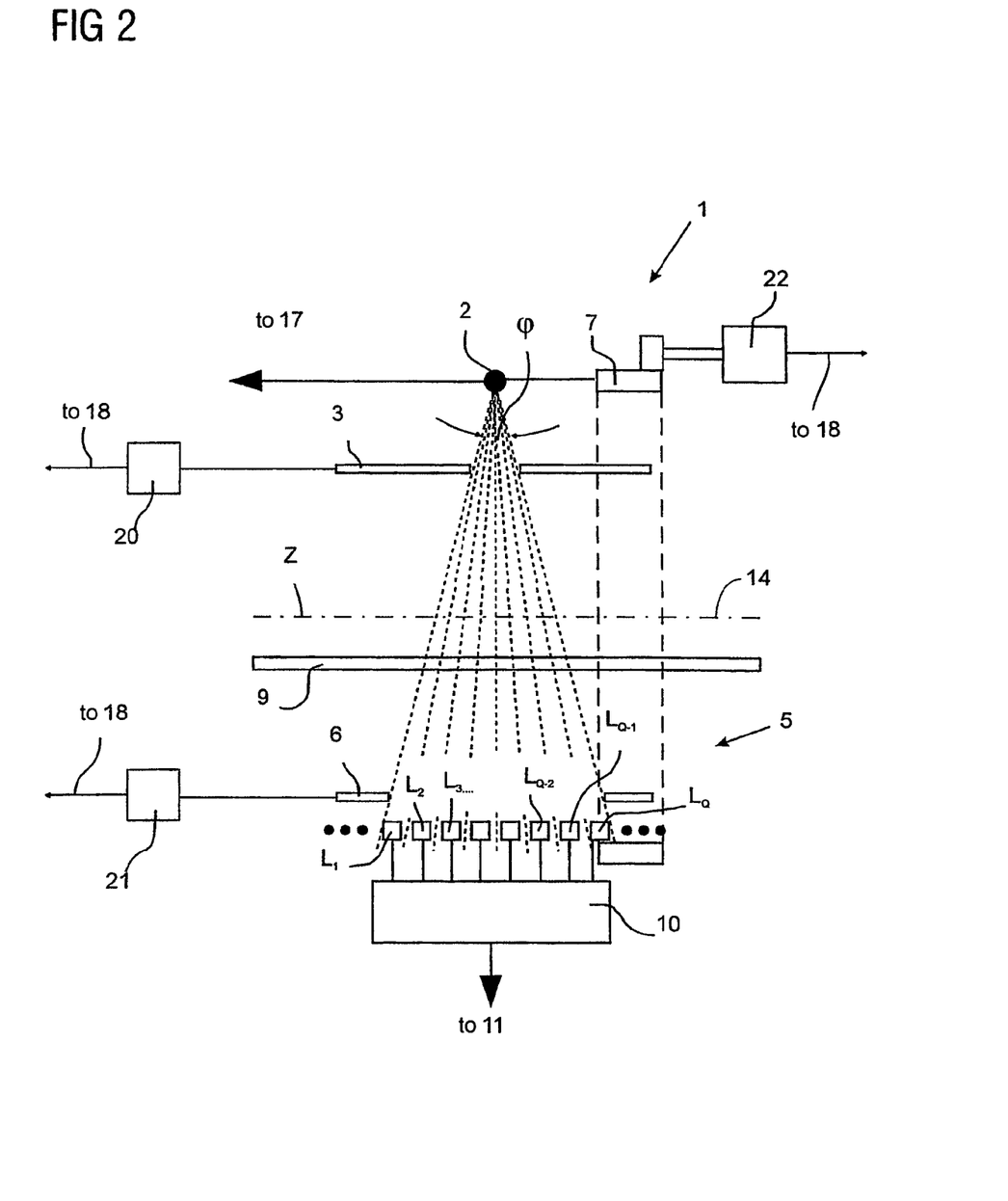
FIG. 2 shows a longitudinal section through the multirow CT from FIG. 1.

FIGS. 1 and 2 show a partially perspective illustration of a third-generation multirow CT unit suitable for carrying out the method according to at least one embodiment of the invention. The measuring arrangement (=Gantry) denoted by 1 has an x-ray source 2 with a beam diaphragm 3 in front thereof and near the source. The two-dimensionally constructed array with a number of rows and columns of detector elements forms the detector system 5 and is represented in section in FIG. 2 with a beam diaphragm 6 in front thereof and near the detector.

For the purpose of better clarity, only eight rows $L_1$ to $L_Q$ of detector elements 4 are illustrated in FIG. 1. However, the detector system 5 can also have another, preferably greater, number of rows without departing from the scope of the invention. Another two-dimensional arrangement of the detectors is likewise also possible.

The X-ray source 2 with the radiation diaphragm 3, on the one hand, and the detector system 5 with the radiation diaphragm 6, on the other hand, are arranged opposite each other on a rotary frame 7 in such a way that a pyramidal X-ray beam which, during the operation of the CT unit, emanates from the X-ray source 2 and is collimated by the settable radiation diaphragm 3 and whose edge rays are designated by 8, strikes the detector system 5. In the process, the radiation diaphragm 6 can be set to correspond to the cross section, set by means of the radiation diaphragm 3, of the X-ray beam in such a way that, in accordance with different operating modes, only that area of the detector system 5 that is struck directly by the X-ray beam is exposed. In FIGS. 1 and 2, only eight rows of detector elements 4 are used, the further rows indicated by dots are covered by the radiation diaphragm 6 and are therefore inactive.

The X-ray beam has a cone angle $\phi$ which is the opening angle of the X-ray beam in a plane containing the system axis Z and the focus F. The opening angle of the X-ray beam in a plane lying at right angles to the system axis Z and containing the focus F (fan opening angle) is $2\beta_{max}$.

The rotary frame 7 can be set rotating about a system axis designated by Z by means of a drive device 22. The system axis Z runs parallel to the z-axis of a three-dimensional rectangular coordinate system illustrated in FIG. 1.

The columns of the detector system 5 likewise run in the direction of the z-axis, while the rows run transversely with respect to the system axis Z.

In order to be able to bring an examination object, for example a patient, into the beam path of the X-ray beam, a bearing device 9 is provided, which can be displaced parallel to the system axis Z, that is to say in the direction of the z-axis, specifically in such a way that there is synchronization between the rotational movement of the rotary frame 7 and the translational movement of the bearing device, with the effect of producing a spiral movement of the focus and of a corotating detector relative to the examination object. The ratio between translational and rotational speeds can be set by a desired value for the feed H of the bearing device 9 being selected per rotation of the rotary frame.

It is therefore possible for a volume of an examination object which is located on the bearing device 9, to be examined in the course of volume scanning, it being possible for the volume scanning to be undertaken in the form of spiral scanning in such a way that, with simultaneous rotation of the measuring unit 1 and translation of the bearing device 9, a multiplicity of projections from various projection directions are recorded by way of the measuring unit per revolution of the measuring unit 1. During the spiral scanning, the focus F of the X-ray source is moved relative to the bearing device 9 on a spiral path S about the examination object.

Measured data read out in parallel from the detector elements of each active row of the detector system 5 during the spiral scanning, and corresponding to the individual projections in cone beam geometry, are subjected to digital/analog conversion in a data conditioning unit 10, are serialized and transmitted to an image computer 11.

After the measured data have been preprocessed in a preprocessing unit 12 of the image computer 11, the resulting data stream passes to a volume image reconstruction unit 13, which uses the measured data to reconstruct images of the desired volume of the examination object by way of the computing operation described later. Both in the preprocessing unit 12 of the image computer 11 and in the volume image reconstruction unit 13, programs or program modules are stored by which the method according to at least one embodiment of the invention can be carried out in order to generate CT images with the aid of a 3D image reconstruction method.

The CT images are assembled from voxels (voxel=volume element) assembled like a grid, the voxels being assigned to the respective image volume, each voxel being assigned a CT number in Hounsfield Units (HU), and it being possible for the individual voxels to be displayed in accordance with a CT number/gray value scale in a gray value corresponding to the respective CT number. The image volume can be visualized in different ways. In a simple form, arbitrary planes can be displayed in an arbitrary orientation as tomograms. However, there are also more complex methods that visualize the entire volume. The shaded surface display (SSD) and volume rendering (VR) may be mentioned here by way of example. The SSD calculates for a settable threshold value an isosurface for which the image volume has the threshold value. The isosurface can be displayed on a screen with the aid of methods of computer graphics. In the case of VR, each voxel is assigned settable optical properties such as opacity and color in accordance with its value. Artificial views of the objects thus defined are calculated with the aid of methods of computer graphics.

Images are calculated by a visualization unit 15 from the volume data reconstructed by the image reconstruction unit 13 and are displayed on a display unit 16, for example, a monitor connected to the image computer 11.

The X-ray source 2, for example an X-ray tube, is supplied by a generator unit 17 with the requisite voltages and currents, for example the tube voltage U.

In order to be able to set the latter to the respectively requisite values, the generator unit 17 is assigned a control unit 18 with a keyboard 19, which permits the values to be set as required. It is to be noted in this regard that in addition to the keyboard 19 it is also possible to provide other known input devices such as mouse, joystick or else voice input.

In addition, the operation and control of the CT unit apart from this is carried out by use of the control unit 18 and the keyboard 19, which is illustrated by the fact that the control unit 18 is connected to the image computer 11.

Amongst other things, the number of the active rows of detector elements 4, and therefore the position of the radiation diaphragms 3 and 6, can be set, for which purpose the control unit 18 is connected to the adjustment units 20 and 21 assigned to the radiation diaphragms 3 and 6. In addition, the rotation time $\tau$ can be set, which is the time needed by the rotary frame 7 for a complete revolution and which is illustrated by the fact that the drive unit 22 associated with the rotary frame 7 is connected to the control unit 18.

Figure 3:
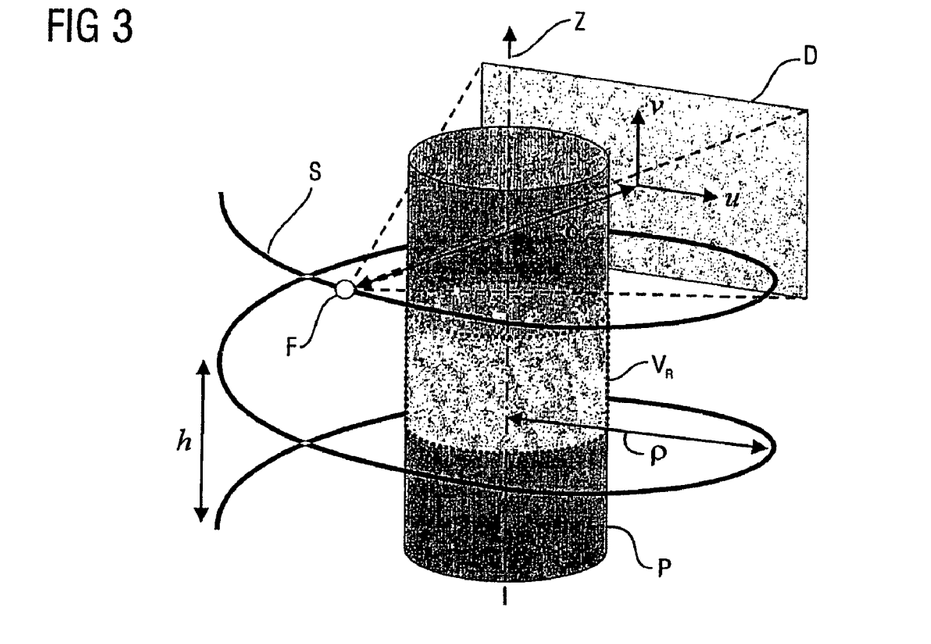
FIG. 3 shows illustrations of the recording geometry of a spiral CT unit.

The recording geometry of the spiral CT unit from FIGS. 1 and 2 is illustrated schematically in FIGS. 3 and 4, the detector being reproduced only in a planar fashion here for the sake of simplicity. The radiation source moves with its focus F along a spiral track S of pitch h, which corresponds to the bed feed, in a fashion rotating about an elongated examination object P, and in the direction of the system axis Z. In this process, the radiation intensity of the rays penetrating the examination object P is measured and collected on the detector D situated opposite. A volume $V_R$ to be reconstructed is embedded within the examination object P.

In order to reconstruct a volumetric image from the measured data, the latter must be filtered, and the filtered data must subsequently be back-projected in three dimensions in order to generate a volumetric image of the examination object, the volumetric image then representing absorption values, obtained from the data, of the voxels V, belonging to the volume of the examination object, for the radiation of the beam.

Thus, consideration of the reconstruction method shows that the cone beams from all focal positions that cut an image voxel V and are measured on the detector surface contribute to the reconstruction of the voxel V. The focal angular range A(V) with useful projection data is therefore a coherent angle interval, and is given by $$A(V)=[\alpha_0(V),\alpha_1(V)].$$

Figure 5:
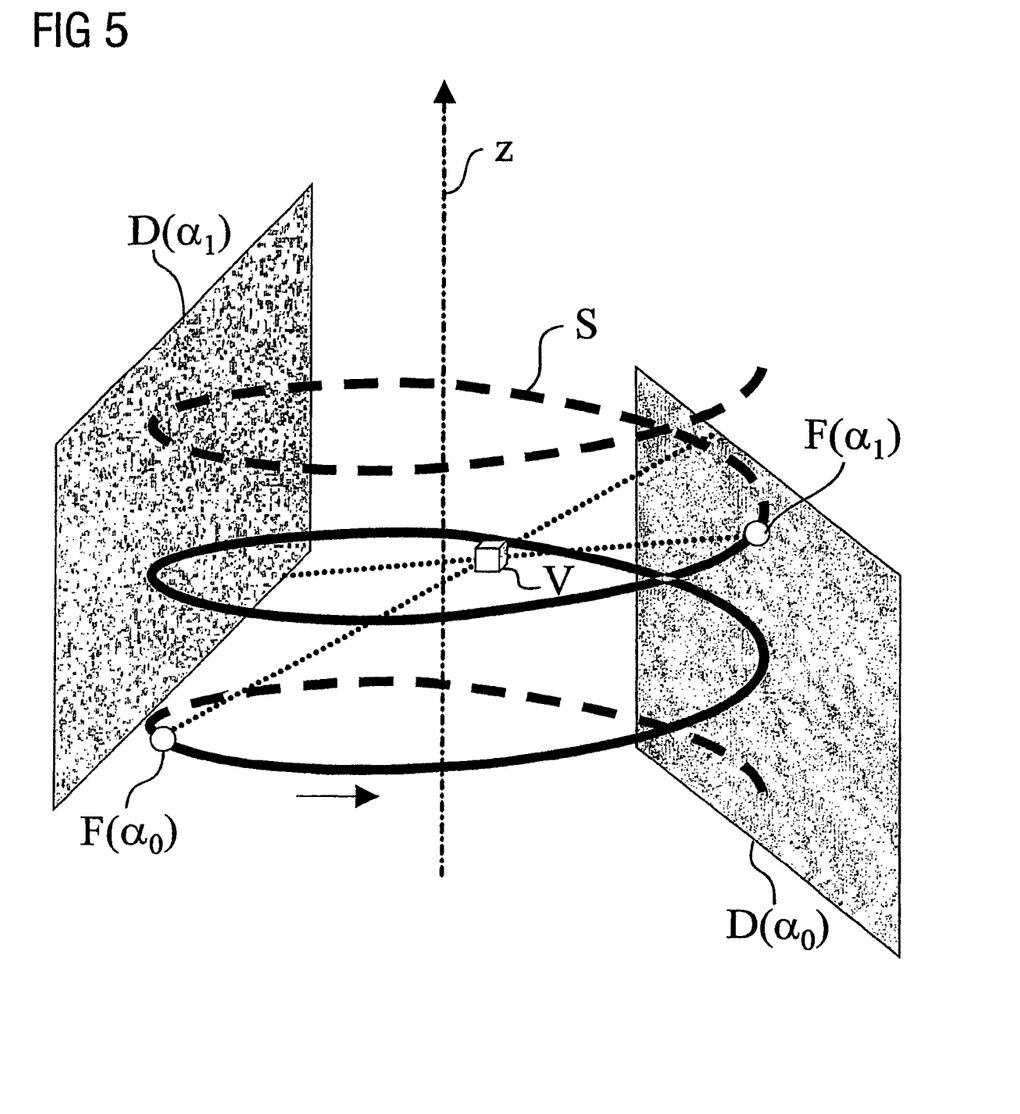
FIG. 5 shows an illustration of the angular interval A(V).

FIG. 5 illustrates this angular interval A(V). It is assumed in this illustration without limitation of generality that the spiral track is traversed by focus and detector in a counter-clockwise sense. The source position $F(\alpha_0)$ is distinguished in that the conical projection of the voxel V firstly strikes the detector surface $D(\alpha_0)$ corresponding to the source position F($\alpha_0$), specifically the upper edge of the detector. In the further course of data acquisition, the conical projection of the voxel V migrates over the detector surface until it leaves the detector at the lower edge in the case of the focal position F($\alpha_1$). All the projections in the angular interval A(V) between $\alpha_0$ and $\alpha_1$ contribute to the reconstruction of the image voxel V.

For example, the associated detector images can now be processed as follows:

The first step is for the detector image to be subjected to a cosine weighting known per se, in order to take account of the oblique radiation present owing to the cone beam geometry.

Subsequently, all the detector data are collected per voxel V considered, this being done along a straight line that runs through the cone beam projection of the voxel V and is aligned in the direction of projection $\vec{t}$ of the spiral tangent $S_t$. If these data are not originally available, the required data are obtained from neighboring original data via an interpolation method.

This is followed by the approximate weighting for the purpose of compensating data redundancies. For this purpose, the projection angle $\theta=\alpha+\beta$ and the parallel coordinate $p=R_F\cdot\sin\beta$ (with $R_F$ being the radius of the focal track) can be determined from the focal angle $\alpha$ and the fan angle $\beta$, the cone angle being neglected. Two measuring beams $S_a$ and $S_b$ are considered as redundant in this case when it holds that ($\theta_a=2k\cdot\pi+\theta_b$ and $p_a=p_b$) or ($\theta_a=(2k+1)\cdot\pi+\theta_b$ and $p_a=-p_b$) and k represents an arbitrary natural number. If redundant data are available, they can be multiplied by the generalized Parker weights. It is to be noted in this regard that the measuring beams defined as approximately redundant because of the different inclination to the z-axis (cone angle) are different and therefore not redundant. However, this approximation of the data redundancy can be extended relatively far because of the generally relatively small cone angle.

Ramp filtering with a suitable smoothing window can be used to filter the values, and the 3D back projection into the voxel V can be performed with the aid of a distance weighting known per se.

It may be pointed out in addition that the method according to at least one embodiment of the invention is suitable for CT units that are operated with simultaneously circulating focus/detector pairs. It is further suitable for CT units that have annularly arranged detectors that are fixed in the direction of rotation and where only the focus rotates and the focus and detector can move in the z-direction.

CITED LITERATURE

[1] M. Kachelrieβ, S. Schaller, and W. A. Kalender, "Advanced single-slice rebinning in cone-beam spiral CT", Med. Phys. 27 (2000) 754-772

[2] S. Schaller, K. Stierstorfer, H. Bruder, K. Kachelrieβ, and T. Flohr, "Novel approximate approach for high-quality image reconstruction in helical cone beam CT at arbitrary pitch", Proceedings SPIE 4322 (2001) 113-127

[3] K. Stierstorfer, T. Flohr, H. Bruder, "Segmented Multiple Plane Reconstruction—A Novel Approximate Reconstruction Scheme for Multislice Spiral CT", Institute of Physics Publishing, Physics in Medicine and Biology, Phys. Med. Biol. 47 (2002) 2571-2581.

[4] Laid-Open Patent Application DE 101 58 927 A1.

[5] K. Sourbelle, IMP, Erlangen University, Dissertation, Date of Examination Mar. 25, 2002, pages 33-37.

[6] Avinash C. Kak, and Malcolm Slaney, Principles of Computerized Tomographic Imaging", IEEE Press, New York, 1987, pp. 49-112.

[7] K. Sourbelle, H. Kudo, G. Lauritsch, K. C. Tam, M. Defrise, and F. Noo, "Performance Evaluation of Exact Cone-Beam Algorithms for the Long-Object Problem in Spiral Computed tomography", Proceedings of Intern. Meeting on Fully 3-D Image Reconstruction in Radiology and Nuclear Medicine, Pacific Grove, Calif., USA, Oct. 30-Nov. 2, 2001, pp. 153-156.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for generating images in computed tomography using 3D image reconstruction, the method comprising:
    scanning an examination object by moving a focus on a spiral focal track about the examination object using a conical beam emanating from the focus and using a detector for detecting the beam, the detector supplying output data corresponding to the detected radiation; and
    reconstructing image voxels from the scanned examination object from the output data and reproducing attenuation coefficients of the respective voxel, each image voxel being reconstructed separately from projection data that include a projection angular range of at least 180°, whereby a measured value filtered for each image voxel is accumulated only on the respective voxel, and an approximate weighting taking place for each voxel considered in order to normalize the projection data used relating to the respective voxel, wherein
    the approximate weighting takes place on the projection data after interpolating the projection data and before filtering the projection data, the approximate weighting using voxel individual Parker weights.

2. The method as claimed in claim 1, wherein reconstructing the image voxels includes using all the detector data along a straight line that runs through the cone beam projection of each image voxel and is aligned in a direction of the projection of the spiral tangent.

3. The method as claimed in claim 1, wherein the image data of the detector image are subjected to a cosine weighting for compensating oblique radiation.

4. The method as claimed in claim 1, wherein data not directly available are obtained from the available data by interpolation from neighboring detector data.

5. The method as claimed in claim 1, wherein during a weighting for compensating a data redundancy, two measuring beams (Sa, Sb) are regarded as redundant precisely when holding that: ($\theta_a=(2k\cdot\pi+\theta_b$ and $p_a=p_b$) or ($\theta_a=(2k+1)\cdot\pi=\theta_b$ and $p_a=-p_b$), where
    k represents an arbitrary natural number,
    θ represents a projection angle, and
    p represents a distance from a z-axis.

6. The method as claimed in claim 5, wherein the redundant data are multiplied by generalized Parker weights.

7. The method as claimed in claim 1, wherein a ramp filter that is manipulated with the aid of a smoothing window is applied to the normalized projection data.

8. The method as claimed in claim 1, wherein a distance weighting is performed for the purpose of 3D back projection into the voxel considered.

9. The method as claimed in claim 1, wherein the method is used for cardiac computer tomography by at least one of selecting, weighting and sorting measured data in accordance with the movement phases of an examined heart.

10. The method as claimed in claim 2, wherein the image data of the detector image are subjected to a cosine weighting for compensating oblique radiation.

11. The method as claimed in claim 1, wherein data not directly available are obtained from the available data by interpolation from neighboring detector data.

12. The method as claimed in claim 2, wherein during the weighting for compensating a data redundancy, two measuring beams (Sa, Sb) are regarded as redundant precisely when holding that: $(\theta_a = (2k \cdot \pi + \theta_b$ and $p_a = p_b)$ or $(\theta_a = (2k+1) \cdot \pi = \theta_b$ and $p_a = -p_b)$, where k represents an arbitrary natural number, θ represents a projection angle, and p represents a distance from a z-axis.

13. The method as claimed in claim 12, wherein the redundant data are multiplied by generalized Parker weights.

14. The method as claimed in claim 1, wherein the projection angular range is a range from at least 180° to less than 360°.

15. A CT unit for scanning an examination object, comprising:

a beam emanating from at least one focus and a detector array having a multiplicity of distributed detector elements for detecting the rays of the beam, the at least one focus being movable relative to the examination object on at least one focal track that runs around the examination object and a detector array situated opposite;

means for collecting detector data, filtering and 3D back projection; and means for processing the collected data being fashioned in such a way to carry out the method as claimed in claim 1.

16. A computer readable medium configured to execute the method as claimed in claim 1.

17. A CT unit for scanning an examination object, comprising:

a beam emanating from at least one focus and a detector array having a multiplicity of distributed detector elements for detecting the rays of the beam, the at least one focus being movable relative to the examination object on at least one focal track that runs around the examination object and a detector array situated opposite; and means for reconstructing image voxels from the scanned examination object from the output data and reproducing attenuation coefficients of the respective voxel, each image voxel being reconstructed separately from projection data that include a projection angular range of at least 180°, whereby a measured value filtered for each Image voxel is accumulated only on the respective voxel, and an approximate weighting taking place for each voxel considered in order to normalize the projection data used relating to the respective voxel, wherein the approximate weighting takes place on the projection data after interpolating the projection data and before filtering the projection data, the approximate weighting using voxel individual Parker weights.

* * * * *